(12) United States Patent
Khouri et al.

(10) Patent No.: US 11,992,429 B2
(45) Date of Patent: *May 28, 2024

(54) RIGIDIFYING BRACE

(71) Applicant: Lipocosm, LLC, Key Biscayne, FL (US)

(72) Inventors: Roger K. Khouri, Key Biscayne, FL (US); Khalil R. Khouri, Key Biscayne, FL (US); Thomas Morgan Biggs, Jr., Houston, TX (US)

(73) Assignee: LIPOCOSM, LLC, Key Biscayne, FL (US)

( * ) Notice: Subject to any disclaimer, the term of this patent is extended or adjusted under 35 U.S.C. 154(b) by 40 days.

This patent is subject to a terminal disclaimer.

(21) Appl. No.: 17/989,664

(22) Filed: Nov. 17, 2022

(65) Prior Publication Data

US 2023/0084629 A1 Mar. 16, 2023

Related U.S. Application Data

(63) Continuation of application No. 17/268,302, filed as application No. PCT/US2019/054890 on Oct. 4, 2019, now Pat. No. 11,504,260.

(Continued)

(51) Int. Cl.
  *A61F 5/03* (2006.01)
  *A41C 3/00* (2006.01)
  *A61F 13/14* (2006.01)

(52) U.S. Cl.
  CPC .............. *A61F 5/03* (2013.01); *A41C 3/0064* (2013.01); *A61F 13/145* (2013.01)

(58) Field of Classification Search
  CPC ...... A61F 5/03; A61F 13/145; A61F 5/05833; A61F 13/20; A41C 3/0064; A61B 5/6862;
  (Continued)

(56) References Cited

U.S. PATENT DOCUMENTS

| 936,434 A | 10/1909 | Eganhouse |
| 3,382,867 A | 5/1968 | Reaves |
| (Continued) | | |

FOREIGN PATENT DOCUMENTS

| CA | 2 827 067 | 8/2012 |
| CH | 396 311 | 7/1965 |
| (Continued) | | |

OTHER PUBLICATIONS

English translation of Liu (CN 108042862 A) (Year:2018).
(Continued)

*Primary Examiner* — Tarla R Patel
(74) *Attorney, Agent, or Firm* — Neil D. Gershon

(57) ABSTRACT

A passive stent for retaining an organ in an expanded state configured to adhere and substantially conform to an external surface of the organ may include an inner layer, an outer layer, and a middle layer that is enclosed by the inner layer and the outer layer, comprising a plurality of components configured to interlock and maintain the organ in an expanded state upon application of a vacuum. A method for retaining an organ in an expanded state may include applying at least one force to the organ to place the organ in the expanded state; applying a passive stent to an external surface of the organ; and applying a vacuum to the passive stent sufficient to cause a plurality of components of at least one layer of the passive stent to interlock, where the at least one layer is configured to maintain the organ in the expanded state after interlocking.

5 Claims, 13 Drawing Sheets

Related U.S. Application Data

(60) Provisional application No. 62/741,516, filed on Oct. 4, 2018.

(58) Field of Classification Search
CPC .... A61B 17/12118; A61B 2017/32096; A61B 17/12159
See application file for complete search history.

(56) References Cited

U.S. PATENT DOCUMENTS

| | | | |
|---|---|---|---|
| 3,785,369 | A | 1/1974 | Tallent |
| 4,635,618 | A | 1/1987 | Munz |
| 4,848,364 | A * | 7/1989 | Bosman .............. A61F 5/05833 128/850 |
| 5,415,620 | A | 5/1995 | Chen |
| 5,536,233 | A | 7/1996 | Khouri |
| 5,662,583 | A | 9/1997 | Khouri |
| 5,676,634 | A | 10/1997 | Khouri |
| 5,695,445 | A | 12/1997 | Khouri |
| 5,701,917 | A | 12/1997 | Khouri |
| 6,042,537 | A | 3/2000 | Kaiser |
| 6,074,399 | A | 6/2000 | Wallace et al. |
| 6,478,656 | B1 | 11/2002 | Khouri |
| 6,500,112 | B1 | 12/2002 | Khouri |
| 6,558,314 | B1 | 5/2003 | Adelman |
| 6,641,527 | B2 * | 11/2003 | Khouri .................. A61B 90/02 600/38 |
| 6,699,176 | B1 | 3/2004 | Khouri |
| 6,949,067 | B1 | 9/2005 | Dann et al. |
| 7,909,805 | B2 | 3/2011 | Weston |
| 7,929,805 | B2 | 4/2011 | Wang et al. |
| 8,485,192 | B2 | 7/2013 | Davidson et al. |
| 9,066,795 | B2 | 6/2015 | Khouri et al. |
| 9,498,565 | B2 | 11/2016 | Nowroozi et al. |
| 9,522,058 | B2 | 12/2016 | Khouri et al. |
| 10,433,947 | B2 | 10/2019 | Khouri et al. |
| 10,603,161 | B2 | 3/2020 | Horne et al. |
| 11,504,260 | B2 * | 11/2022 | Khouri .............. A61F 13/145 |
| 11,540,894 | B2 * | 1/2023 | Khouri ...................... A61F 2/52 |
| 2001/0031911 | A1 | 10/2001 | Khouri |
| 2003/0073951 | A1 | 4/2003 | Morton et al. |
| 2005/0008669 | A1 | 1/2005 | Chen |
| 2005/0059853 | A9 | 3/2005 | Kochamba |
| 2005/0101222 | A1 | 5/2005 | Cope |
| 2005/0245850 | A1 | 11/2005 | Freyre et al. |
| 2005/0267386 | A1 | 12/2005 | Copelan |
| 2006/0106334 | A1 | 5/2006 | Jordan et al. |
| 2007/0055179 | A1 | 3/2007 | Deem |
| 2007/0149991 | A1 | 6/2007 | Mulholland |
| 2009/0042477 | A1 | 2/2009 | Redenius |
| 2009/0177134 | A1 | 7/2009 | Timothy |
| 2011/0251602 | A1 | 10/2011 | Anderson |
| 2011/0313412 | A1 | 12/2011 | Kim et al. |
| 2012/0310126 | A1 * | 12/2012 | Bureau ............... A61F 5/05833 602/6 |
| 2014/0094722 | A1 | 4/2014 | Wu |
| 2014/0144450 | A1 | 5/2014 | Aarestad |
| 2014/0288646 | A1 | 9/2014 | Khouri et al. |
| 2014/0378946 | A1 | 12/2014 | Thompson |
| 2015/0328380 | A1 | 11/2015 | Furrer et al. |
| 2016/0000551 | A1 | 1/2016 | Khouri et al. |
| 2016/0324666 | A1 | 11/2016 | Barberio |
| 2017/0196756 | A1 | 7/2017 | Palomaki |
| 2017/0296422 | A1 | 10/2017 | Park et al. |
| 2017/0341334 | A1 * | 11/2017 | Corrigan ................. B32B 15/12 |
| 2018/0021492 | A1 | 1/2018 | Furrer et al. |
| 2020/0375839 | A1 | 12/2020 | Kim et al. |
| 2020/0405925 | A1 | 12/2020 | Koster et al. |
| 2021/0046227 | A1 | 2/2021 | Bakker-Van Der Kamp et al. |
| 2021/0060220 | A1 | 3/2021 | Chang et al. |
| 2021/0220535 | A1 | 7/2021 | Ochiai et al. |

FOREIGN PATENT DOCUMENTS

| | | |
|---|---|---|
| CN | 103689822 | 4/2014 |
| CN | 108042862 | 5/2018 |
| EP | 2 377 475 | 10/2011 |
| JP | H 1052886 | 2/1998 |
| WO | WO 01/58361 | 8/2001 |
| WO | WO 2005/079612 | 9/2005 |
| WO | WO 2017/165215 | 9/2017 |
| WO | WO 2017/220997 | 12/2017 |
| WO | WO 2020/073021 | 4/2020 |

OTHER PUBLICATIONS

PCT/US2019/0654890 International Search Report (dated Dec. 23, 2019).

PCT/US2021/060680 International Search Report (dated Feb. 18, 2022).

Supplementary European Search Report Application No. EP 13 78 5140 dated Feb. 18, 2016.

Supplementary European Search Report Application No. EP 19 86 8805 dated Nov. 19, 2021.

www.amazon.com/Motherlove-Certified-Organic-Cracked-Nursing/dp/B0007CQ726.

* cited by examiner

RIGIDIFYING BRACE

CROSS-REFERENCE TO RELATED APPLICATIONS

This application is a continuation of Ser. No. 17/268,302, filed Feb. 12, 2021, which is a 371 of international application no. PCT/2019/054890, filed Oct. 4, 2019, which claims the benefit of priority of U.S. Provisional Patent Application No. 62/741,516, filed Oct. 4, 2018. The entire contents of each of these applications are incorporated herein by reference.

TECHNICAL FIELD

The present disclosure relates to a rigidifying brace and corresponding methods for retaining an organ in an expanded state.

BACKGROUND

Generally, edema and tissue swelling are considered pathologic conditions to be treated by medical interventions, such as compression garments. However, in some instances, inducing and maintaining a chronic edema state may be beneficial when the desired goal is to ultimately induce tissue augmentation and enlargement. For example, the applicant has previously developed devices and techniques for manipulating and molding soft tissue with active external tissue expanders like the Brava Bra (see, for example, U.S. Pat. Nos. 5,536,233; 5,662,583; 5,676,634; 5,695,445; 5,701,917; 6,478,656; 6,500,112; 6,641,527; and 6,699,176, all of which are incorporated herein by reference) or the external passive expander splint (see, for example, U.S. Pat. Nos. 9,066,795 and 9,522,058, both of which are incorporated herein by reference).

Existing compression bandages apply external compressive forces to soft tissue, which counteract any distention induced by such devices and techniques. For example, laces, straps, or other components may immobilize the soft tissue. Existing passive bandages also often include an adhesive layer that conforms and sticks to the treated body part and a rigidifying layer that stiffens the construct to preserve and maintain the soft tissue until healing ensues. The rigidifying factors in these existing braces often rely on curing or polymerization of a chemical.

SUMMARY

Thus, it may be desirable to develop new devices and techniques for bracing distended tissues and retaining organs in expanded states. The devices and methods disclosed herein may preserve iatrogenically or otherwise induced swollen tissue conditions while remaining passive. In addition, the devices and methods disclosed herein may prevent the natural tendency of distended and expanded tissues and organs to recoil, which may allow for maintaining a potentially beneficial chronic swelling or edema.

Furthermore, the devices and methods disclosed herein may use interlocking materials to rigidify, thereby avoiding certain drawbacks of existing compression bandages. For instance, achieving rigidity by polymerization of a chemical is a one-time, irreversible process, whereas the devices and methods disclosed herein may be used multiple times and at varying degrees of rigidity. Additionally, braces that achieve rigidity induced by physical agents, such as temperature, face mechanical phase variations. In contrast to these prior art processes, embodiments of the present disclosure rely upon air aspiration to interlock the loosely textured components of the rigidifying layer to stiffen it, as depicted in FIG. 1 below.

In the following description, certain aspects and embodiments will become evident. It should be understood that the aspects and embodiments, in their broadest sense, could be practiced without having one or more features of these aspects and embodiments. It should be understood that these aspects and embodiments are merely exemplary.

According to some embodiments, the disclosure provides a passive stent for retaining an organ in an expanded state. In such embodiments, the passive stent may comprise an inner layer; an outer layer; and a middle layer enclosed by the inner layer and the outer layer and comprising a plurality of components configured to interlock upon application of a vacuum. The middle layer may be configured to substantially conform to an external surface of the organ after interlocking. Additionally, the middle layer may be configured to maintain the organ in the expanded state after interlocking.

In such embodiments, the middle layer may comprise at least one of foam or putty. The at least one of foam or putty may be textured and may comprise textured polyurethane and/or textured polybutene.

Additionally or alternatively, the middle layer may comprise a plurality of strips comprising sponge or cellulose.

Additionally or alternatively, the middle layer may comprise at least one fibrous material. For example, the at least one fibrous material may comprise paper, such as sandpaper. Additionally or alternatively, the middle layer may comprise a gel with fibers. In such embodiments, the fibers may comprise at least one polyester.

Additionally or alternatively, the middle layer may comprise a plurality of sheets of malleable fabric.

Additionally or alternatively, the middle layer may comprise a gel with beads. In such embodiments, the beads may comprise microbeads.

In any embodiments described above, the inner layer may be configured to adhere to the organ using surface tension induced upon interlocking of the middle layer. Additionally or alternatively, the inner layer may be configured to adhere to the organ upon application of a vacuum to a volume (e.g., a volume of air) between the inner layer and a surface of the organ. Accordingly, the brace may further comprise a port allowing for application of the vacuum to the volume through at least the inner layer. Additionally or alternatively, the inner layer may be configured to adhere to the organ using at least one adhesive layer between the inner layer and a surface of the organ.

In any embodiments described above, the brace may further comprise a port allowing for application of the vacuum to the middle layer through at least one of the inner layer and the outer layer.

According to some embodiments, the disclosure provides a brassiere. In such embodiments the brassiere may comprise two cups, each configured to support a breast. Each cup may comprise an inner layer; an outer layer; a middle layer enclosed by the inner layer and the outer layer and comprising a plurality of components configured to interlock upon application of a vacuum; and a port configured to allow the application of the vacuum to the middle layer. The middle layer may be configured to substantially conform to an external surface of the breasts after interlocking. Additionally, the middle layer may be configured to maintain the breasts in the expanded state after interlocking.

In such embodiments, the brassiere may further comprise a semi-rigid frame defining peripheries of the two cups and configured to secure the two cups to peripheries of the breasts. Additionally or alternatively, the brassiere may further comprise a peripheral extension surrounding at least a portion of the two cups and configured to block airflow between the inner layer and skin of the breasts. In some embodiments, the extension is shirt-like. Additionally or alternatively, the brassiere may further comprise fabric configured to conform to a torso and block airflow between the inner layer and skin of the breasts. In some embodiments, the fabric conforms to the torso and the breasts.

According to some embodiments, the disclosure provides a method for retaining an organ in an expanded state. In such embodiments, the method may comprise applying at least one force to the organ to place the organ in the expanded state; applying a passive stent to an external surface of the organ, wherein the passive stent comprises at least one layer comprising a plurality of components; and applying a vacuum to the passive stent sufficient to interlock the plurality of components in the at least one layer. The at least one layer may be configured to maintain the organ in the expanded state after interlocking.

In such embodiments, the organ may comprise a breast.

In any embodiments described above, applying the passive stent may comprise adjusting a morphology of the passive stent to substantially conform to a morphology of the external surface.

In any embodiments described above, applying the vacuum may comprise applying suction to a port of the passive stent such that gas is removed from the at least one layer of the passive stent.

Exemplary objects and advantages will be set forth in part in the description that follows, or may be learned by practice of the exemplary embodiments. It is to be understood that both the foregoing general description and the following detailed description are exemplary and explanatory only and are not restrictive of the invention, as claimed.

DETAILED DESCRIPTION

Figure 1:
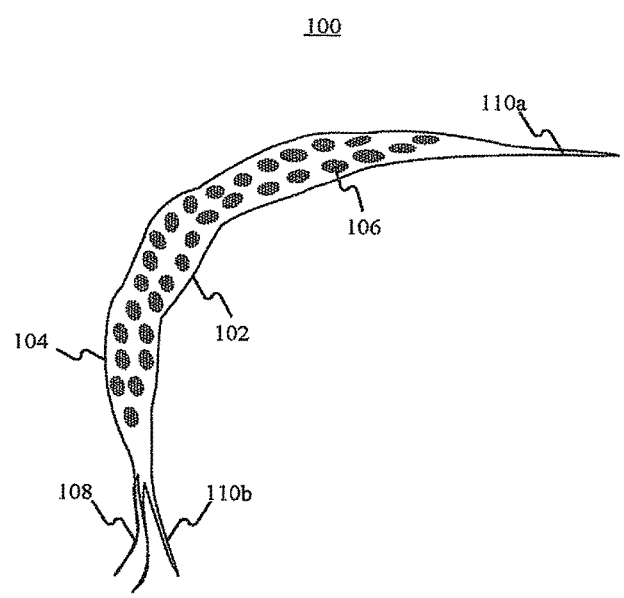
FIG. 1 is a schematic representation of an exemplary rigidifying brace, according to the present disclosure.

According to some embodiments, a passive stent for retaining an organ in an expanded state may comprise an inner layer and an outer layer. The inner layer may contact an external surface of an organ (e.g., skin of a breast), and the outer layer may contact an environment of the organ (e.g., air). The stent may further comprise a middle layer enclosed by the inner layer and the outer layer.

The middle layer may comprise a plurality of components configured to interlock upon application of a vacuum. For example, the middle layer may comprise beads; strips of malleable fabric; strips of carboard, sandpaper, cellulose, or other fibrous material; strips of sponge or other porous material; or the like. The components may be separate from or integral with the inner layer and/or the outer layer. Moreover, the middle layer may further include a fluid (such as air, water, or any other fluid) configured for evacuation via a port through the inner layer and/or the outer layer.

The middle layer may be configured to substantially conform to an external surface of the organ after interlocking. Accordingly, upon aspiration (e.g., using a vacuum) of the fluid (e.g., air), the plurality of components may interlock together and rigidify. Accordingly, the middle layer may be configured to maintain the organ in the expanded state after interlocking.

Any of the rigidifying braces of the present disclosure may be implemented in a brassiere. For example, the cups of a brassiere for breasts may comprise passive stents described herein. In some embodiments, additional semi-rigid frames may surround the stents and contact peripheries of the breasts. Any semi-rigid material, such as one or more polymers or the like, may be used for the frames. Additionally or alternatively, a peripheral shirt-like extension may prevent airflow between the inner layer of the cups and skin of the breasts. For example, the cups may connect to fabric (whether woven, extruded, or the like) configured to conform to a torso and the breasts and block airflow between the inner layer and skin of the breasts.

According to some embodiments, a method for retaining an organ in an expanded state may comprise applying at least one force to the organ to place the organ in the expanded state. For example, the at least one force may be applied using injection, a vacuum, surface tension, or other internal or external force that induces distention in the organ. In some embodiments, the Brava Bra (see, for example, U.S. Pat. Nos. 5,536,233; 5,662,583; 5,676,634; 5,695,445; 5,701,917; 6,478,656; 6,500,112; 6,641,527; and 6,699,176, all of which are incorporated herein by reference) and/or an external passive expander splint (see, for example, U.S. Pat. Nos. 9,066,795 and 9,522,058) may induce the distractive force and, over a period of time, place the organ in the expanded state.

The method may further comprise applying a passive stent to an external surface of the organ. For example, the passive stent may be flexible (as described above) to substantially conform to the external surface of the organ. Additionally, in some embodiments, the passive stent may be further adhered using an adhesive layer and/or a vacuum applied to a volume between the inner layer of the stent and the external surface of the organ.

The method may further comprise applying a vacuum to the passive stent sufficient to cause a plurality of components of at least one layer of the passive stent to interlock. Such application may cause surface tension between the inner layer of the stent and the external surface of the organ such that the former adheres to the latter. The surface tension may be used in lieu of or in addition to the adhesive layer and/or vacuum applied to a volume between the inner layer of the stent and the external surface of the organ described above. Accordingly, the at least one layer may be configured to maintain the organ in the expanded state after interlocking.

In some embodiments, the disclosed devices and methods may prevent the natural tendency of distended and expanded tissues and organs to recoil without relying on curing. Accordingly, the disclosed devices and methods may be more cost-effective than existing passive braces as well as easier to implement by using a vacuum rather than ultraviolet lamps, polymerization chemicals, or other curing implements.

FIG. 1 is a schematic representation of exemplary brace 100. Brace 100 may comprise an inner layer 102, an outer layer 104, and a middle layer 106. As depicted in FIG. 1, brace 100 may be configured to conform to an external surface of an organ, e.g., a breast.

The inner layer 102 may be configured to contact an external surface (e.g., a portion of skin) of an organ (e.g., a breast). Accordingly, inner layer 102 may comprise a biocompatible material, such as one or more polymers compatible with the external surface. The outer layer 104 may be configured to contact the environment of the organ (e.g., the atmosphere). Outer layer 104 may comprise one or more polymers or any other material compatible with the environment.

As further depicted in FIG. 1, brace 100 may substantially conform to the external surface of the organ. Therefore, inner layer 102 and outer layer 104 may be flexible materials, such as flexible polymers, flexible fabrics (e.g., woven or extruded fabrics), or the like. As used herein, "substantially conform" may refer to contact between two surfaces containing air bubbles, obtrusions, imperfections, etc., that are sufficiently small such that one of the surfaces may still apply surface tension to the other of the surfaces. Two surfaces, then, may be termed "substantially conforming" as used herein even if not perfectly contacting each other free of air bubbles, obtrusions, imperfections, etc.

Inner layer 102 and outer layer 104 may enclose a middle layer 106. The middle layer 106 may comprise a textured or fibrous material including fibers or beads (e.g., microbeads) configured to interlock and rigidify upon application of a vacuum. For example, middle layer 106 may comprise strips of paper, such as cardboard or sandpaper, strips of sponge, strips of cellulose, or sheets of fabric amongst a fluid (e.g., air, water, an inert gel, or the like).

Additionally or alternatively, the middle layer may comprise a foamy or porous material configured to interlock and rigidify upon application of a vacuum. For example, middle layer 106 may comprise textured polyurethane, textured polybutene, or the like amongst a fluid (e.g., air, water, an inert gel, or the like).

In some embodiments, the interlocking materials in the middle layer 106 may be structurally part of the inner layer 102 and of the outer layer 104. In some embodiments, as discussed above, inner layer 102 and outer layer 104 may enclose a fluid (e.g., air, water, an inert gel, or the like). Aspiration of that fluid, e.g., through a syringe or a pump, whether mechanical or manual, may collapse the middle layer 106. In general, air aspiration, extraction of a gel or fluid in the middle layer, electromechanical mechanisms such as interlocking magnets or a Velcro-like mechanism, or any other appropriate mechanism may cause the interlocking materials in the middle layer 106 to connect together and rigidify.

Collapse of middle layer 106 may result in the interlocking of the structures comprising middle layer 106. For example, as explained above, the middle layer 106 may comprise textured foam, textured putty, and/or gel with fibers and/or beads configured to interlock and become rigid when a radial thickness of the same is forcefully reduced, e.g., by vacuum or aspiration of fluid in middle layer 106. Additionally or alternatively, interlocking structures of the middle layer 106 may comprise sheets of paper, malleable fabric, or other malleable material configured to become stiff when pressed together, e.g., by forceful removal of air, water, or other ambient fluid in middle layer 106. The expelled fluid may comprise air or another gas such that removal results in a vacuum or may comprise an inert liquid or gel such that removal forces the interlocking components of middle layer 106 together such that the components collectively stiffen.

In some embodiments, the middle layer may have a variable thickness. The variable thickness may improve the adaptability of the middle layer to morphology of the external surface of the organ. For example, the middle layer 106 may comprise polymer foam, e.g. polyurethane or polybutene, having a thickness adjusted by aspiration of air contained therein. Through a controlled reduction of its volume and thickness, e.g., using a vacuum as described above, the middle layer 106 may substantially conform to the morphology of the organ, and the textured foam, fibers, beads, or the like of middle layer 106 may interlock to rigidify and prevent the external surface from recoiling. The stent may also passively impart a distractive force to the organ.

Figure 2:
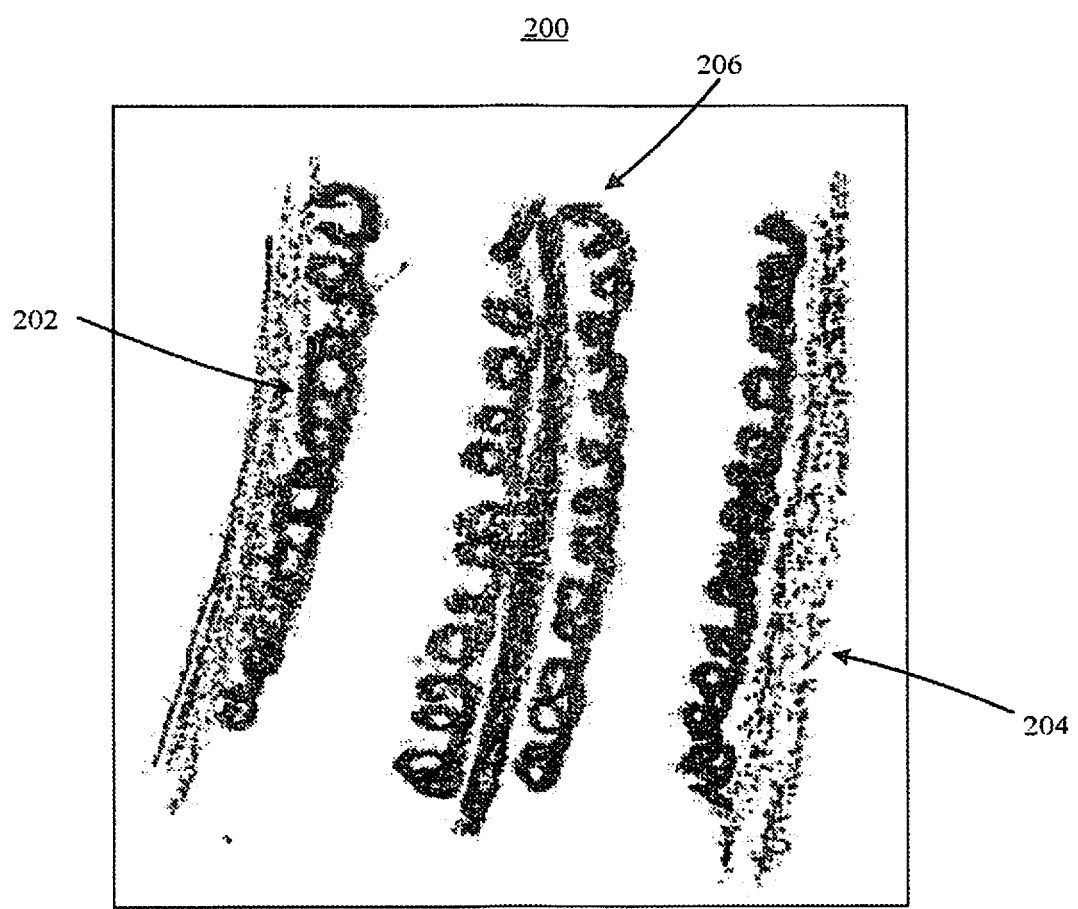
FIG. 2 is a schematic representation of a middle layer of the rigidifying brace of FIG. 1, according to the present disclosure.

FIG. 2 is a schematic representation of a zoomed-in version of exemplary brace 200. For example, brace 100 of FIG. 1 may comprise brace 200 of FIG. 2. As shown in FIG. 2, inner layer 202 of the brace may include textured or rough material and/or ridges, whether random or in a pattern, at least on a portion of inner layer 202 facing middle layer 206. Similarly, outer layer 204 may include textured or rough material and/or ridges, whether random or in a pattern, at least on a portion of outer layer 204 facing middle layer 206.

As further depicted in FIG. 2, middle layer 206 may comprise stacked layers of fibers, strips of paper, sheets of fabric, and/or restrained beads. For example, the fibers may comprise inter-digitating layers, fibers, strips, sheets and/or beads, whether random or in a pattern.

Figure 3A:
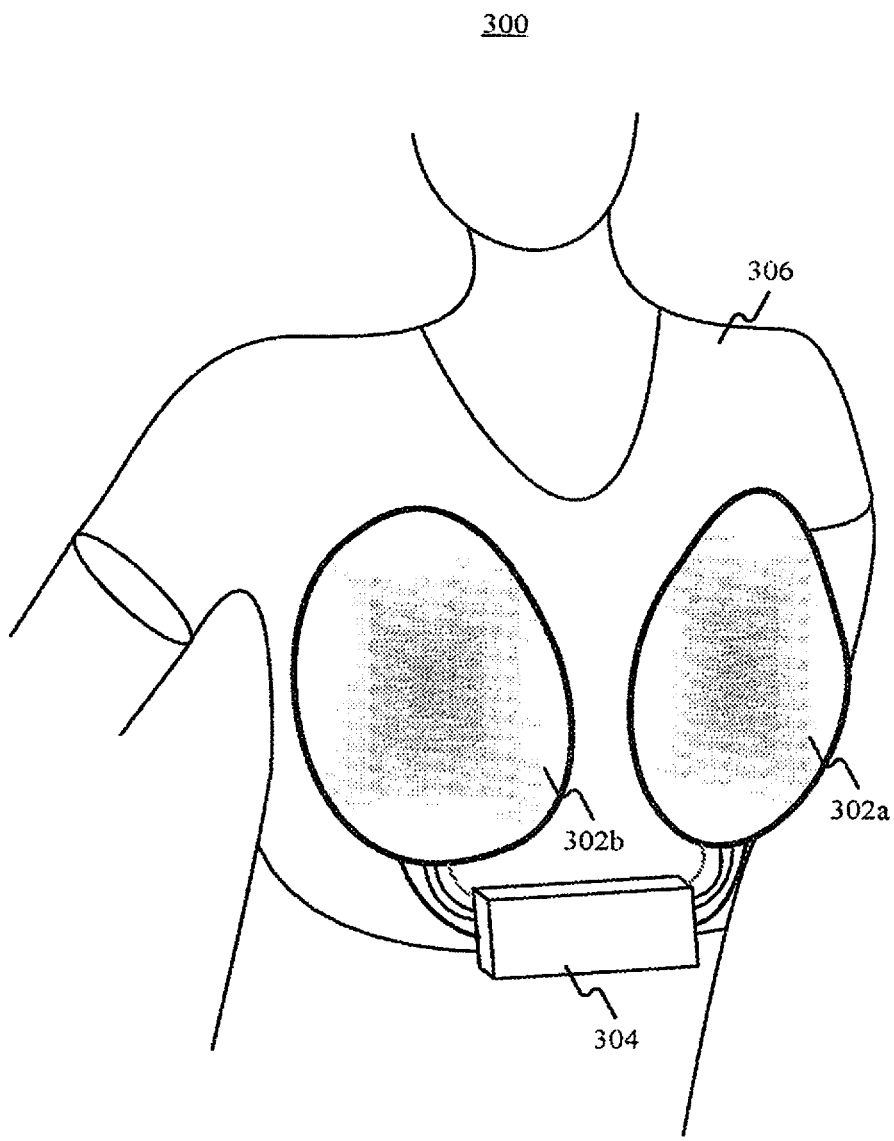
FIG. 3A is a schematic representation of an exemplary brassiere incorporating a rigidifying brace of FIG. 1, according to the present disclosure.
Figure 3B:
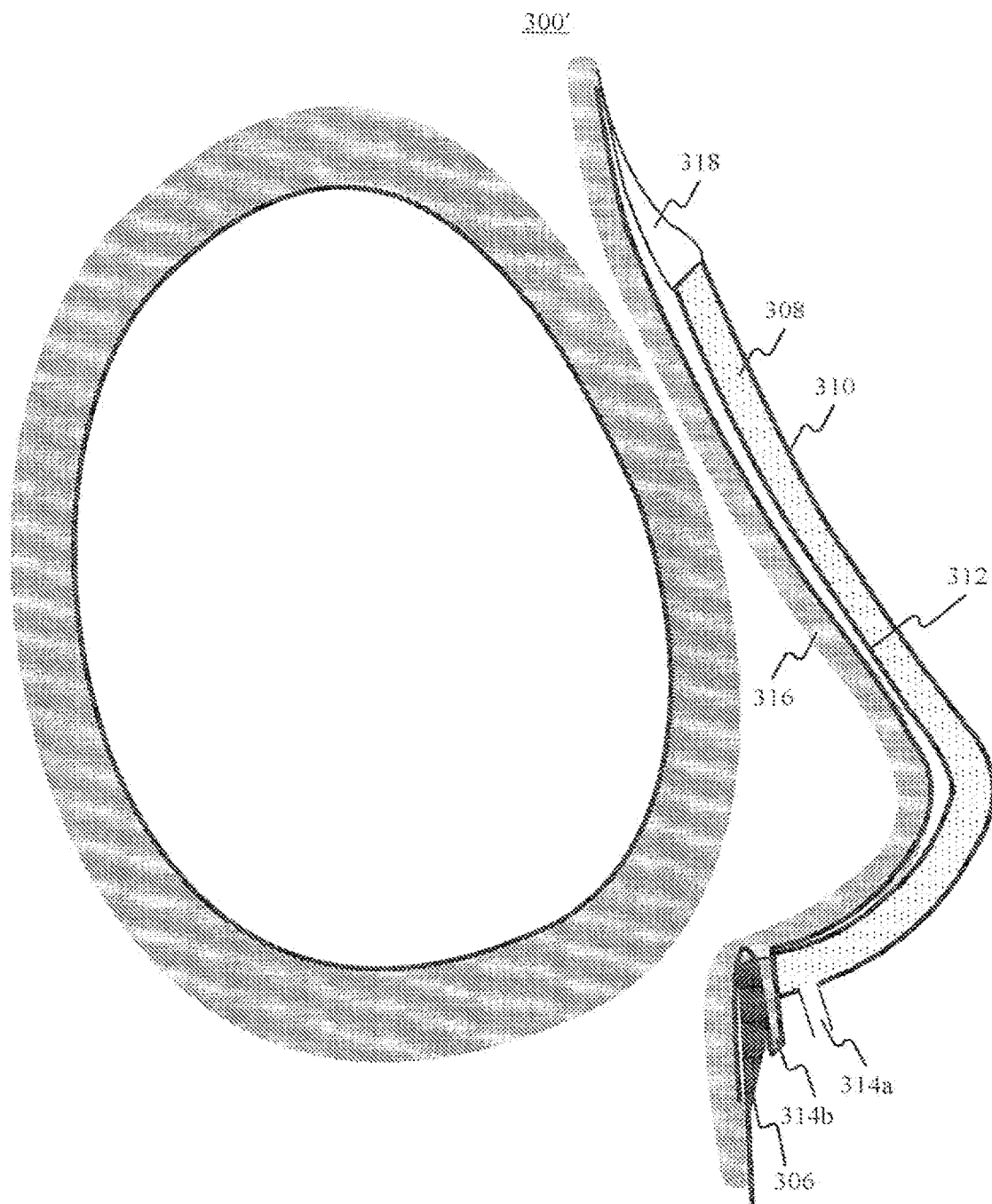
FIGS. 3B and 3C are side views of the exemplary brassiere incorporating a rigidifying brace of FIG. 3A, according to the present disclosure.
Figure 3C:
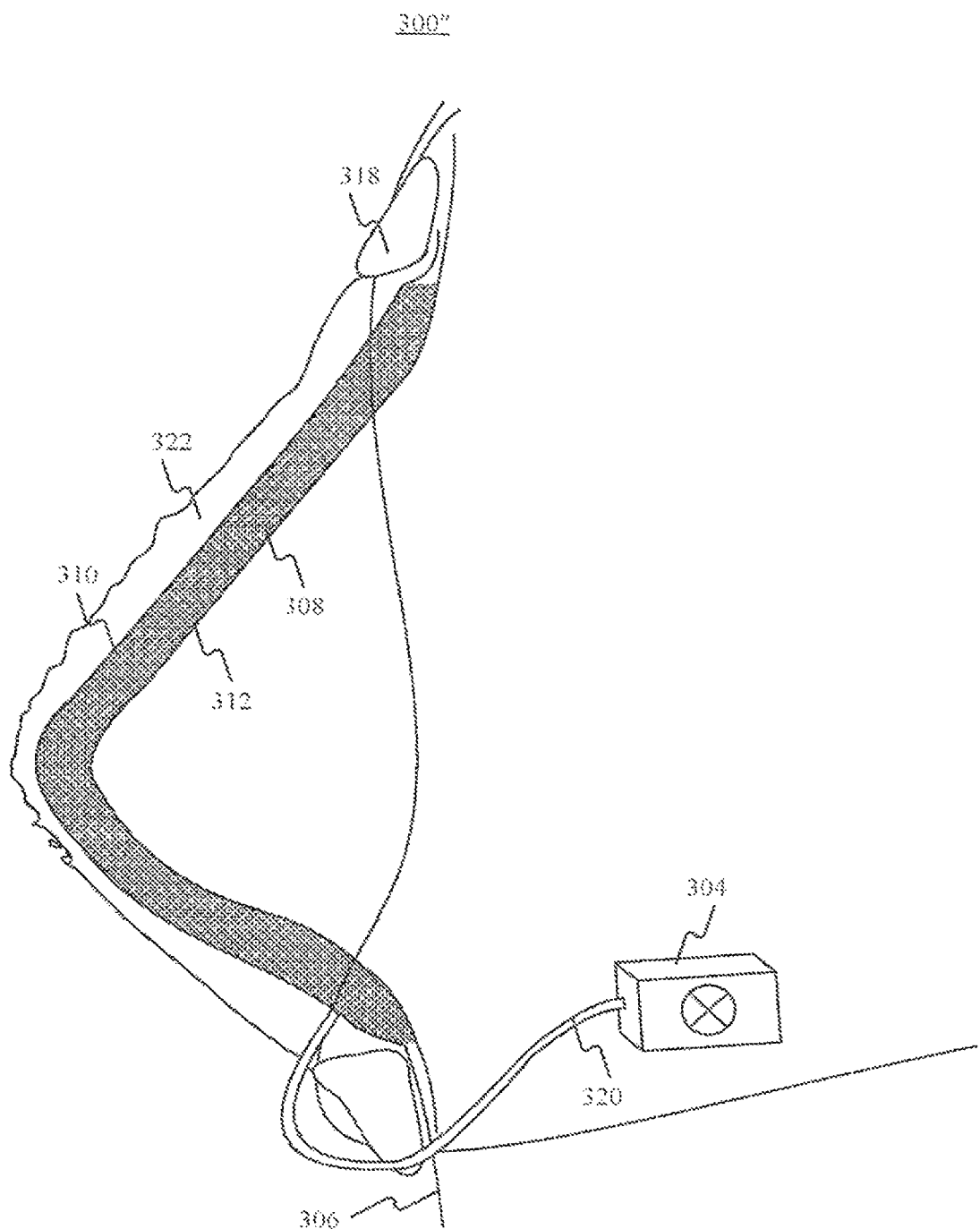

FIG. 3A is a schematic representation of an exemplary brassiere 300 incorporating a rigidifying brace, such as brace 100 of FIG. 1. For example, brassiere 300 may be taken on and off by an individual (e.g., as depicted in FIGS. 3B-3D described below). One or both cups 302a and 302b of the brassiere may comprise a passive stent as described herein (e.g., stent 100 of FIG. 1). The cups may comprise a stretchable material, such as a sheet of fabric (whether woven, extruded, or the like) or other polymer, configured to conform to the morphology of the breasts. Upon forceful expulsion of fluid (such as air, water, or the like) from middle layers of the stents, the cups may rigidify and maintain the shapes and corresponding volumes of the breasts. Moreover, the inner layers of the stents may adhere to the breasts, whether from surface tension between the inner layers and the skin of the breasts, suction from a vacuum applied to a volume between the inner layers and the skin of the breasts, an adhesive layer between the inner layers and the skin of the breasts (e.g., as depicted in FIG. 3B and described below), or a combination thereof.

As further depicted in FIG. 3A, the brassiere 300 may include a control mechanism 304. The control mechanism may include, for example, one or more vacuum pumps (e.g., to activate the middle layer as described above and/or for monitoring and correction of airflow between the inner layers and the skin of the breasts as described below with respect to method 500 of FIG. 5), one or more pressure sensors (e.g., for monitoring airflow between the inner layers and the skin of the breasts as described below with respect to method 500 of FIG. 5), an energy source (e.g., a battery, fuel cell, or the like) for powering the pump(s) and/or sensor(s), and a control mechanism (e.g., a microprocessor for generating commands and/or, a communications interface for receiving commands) for the pump(s) and/or sensor(s).

Moreover, in some embodiments, brassiere 300 may further comprise an extension 306. The extension may comprise fabric or other polymer. As shown in FIG. 3A, extension 306 may surround, at least in part, a torso of which the breasts are part. Accordingly, extension 306 may comprise a shirt-like garment to which cups 302a and 302b are attached (e.g., via sewing, weaving, adhesive, or the like). Moreover, extension 306 may secure cups 302a and 302b to the torso and/or may prevent airflow between the inner layers of the stents comprising the cups and skin of the breasts.

FIGS. 3B and 3C are side views 300' and 300", respectively, of brassiere 300 of FIG. 3A. FIG. 3B further depicts a semi-rigid frame 318 that defines peripheries of cups 302a and 302b. Frame 318 may further bear counterforces on cups 302a and 302b from the breasts and hold active components of cups 302a and 302b (e.g., inner layers and middle layers of stents of cups 302a and 302b) in place against the skin of the breasts. In such embodiments, extension 306 may attach to frame 318 (e.g., via sewing, weaving, adhesive, or the like), which is then attached to cups 302a and 302b (e.g., via sewing, weaving, adhesive, or the like).

FIG. 3B further depicts inner layer 312 of cups 302a and 302b (which may contain textured or rough material and/or ridges, whether random or in a pattern as explained above with respect to FIG. 2) and outer layer 310 of cups 302a and 302b (which may contain textured or rough material and/or ridges, whether random or in a pattern as explained above with respect to FIG. 2). In addition, FIG. 38 depicts middle layer 308 of cups 302a and 302b (which may comprise stacked layers of fibers, strips of paper, sheets of fabric, and/or restrained beads, such as inter-digitating layers, fibers, strips, sheets and/or beads, whether random or in a pattern, as explained above with respect to FIG. 2).

FIG. 3B further depicts an adhesive layer 316, which may comprise tissue glue, pressure sensitive adhesive, and/or other types of biocompatible glue. Some embodiments may omit adhesive layer 316. Such embodiments may use surface tension between the inner layer 312 and the skin of the breast arising after interlocking of the components of middle layer 308 to achieve adherence. Additionally or alternatively, such embodiments may cause adhesion between the inner layer 312 and the skin of the breast by aspirating air in a volume between the inner layer 312 and the skin of the breast and/or by allowing the inner layer 312 to be porous and/or have fine holes such that the vacuum created in the middle layer 308 also adheres the skin of the breasts to the inner layer 312.

Brassiere 300' further includes tubing 314a through outer layer 310 configured to apply a vacuum to middle layer 308 such that the components of middle layer 308 interlock. Some embodiments, such as brassiere 300', may further include tubing 314b through inner layer 312 configured to apply a vacuum to a volume between the inner layer 312 and the skin of the breast (as described above).

FIG. 3C also depicts frame 318 and extension 306, described above with respect to FIG. 3B. As further shown in FIG. 3C, additional fabric (whether woven, extruded, or the like) or other polymers may cover cups 302a and 302b in layer 322. Layer 322 may improve fashionability of brassiere 300". FIG. 3C also depicts control mechanism 304 described above with respect to FIG. 3A. In brassiere 300", control mechanism 304 applies a vacuum to middle layer 308 using tubing 320 through outer layer 310, although in other embodiments tubing 320 may proceed through inner layer 312. Accordingly, the vacuum applied to middle layer 308 may enter through one or more ports passing through inner layer 312 and/or outer layer 310. Similarly, any vacuum applied to a volume between the inner layer 312 and the skin of the breast may enter through one or more ports passing through inner layer 304 (optionally with outer layer 310 as well) and/or frame 310.

Figure 4A:
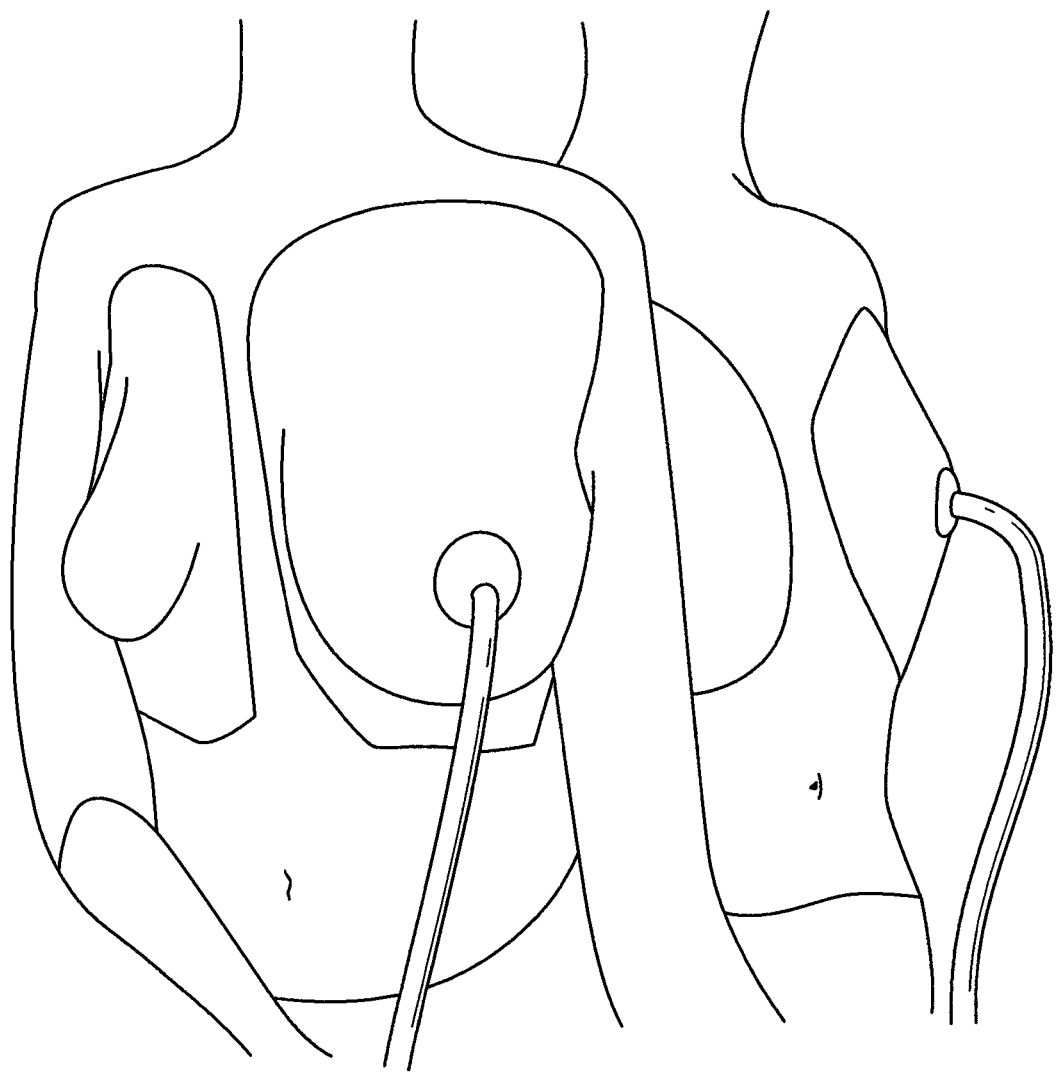
FIGS. 4A, 4B, 4C, 4D, 4E, 4F, and 4G are pictures of one implementation of the exemplary brassiere of FIG. 3A, according to the present disclosure.

FIG. 4A is an image of an exemplary implementation 400 of a brassiere (such as brassiere 300 of FIG. 3) incorporating a rigidifying brace, such as brace 100 of FIG. 1. FIG. 4A includes a vacuum connected via a port through the outer layer of the brassiere to rigidify the middle layer of the stents within the cups of the brassiere.

Figure 4B:
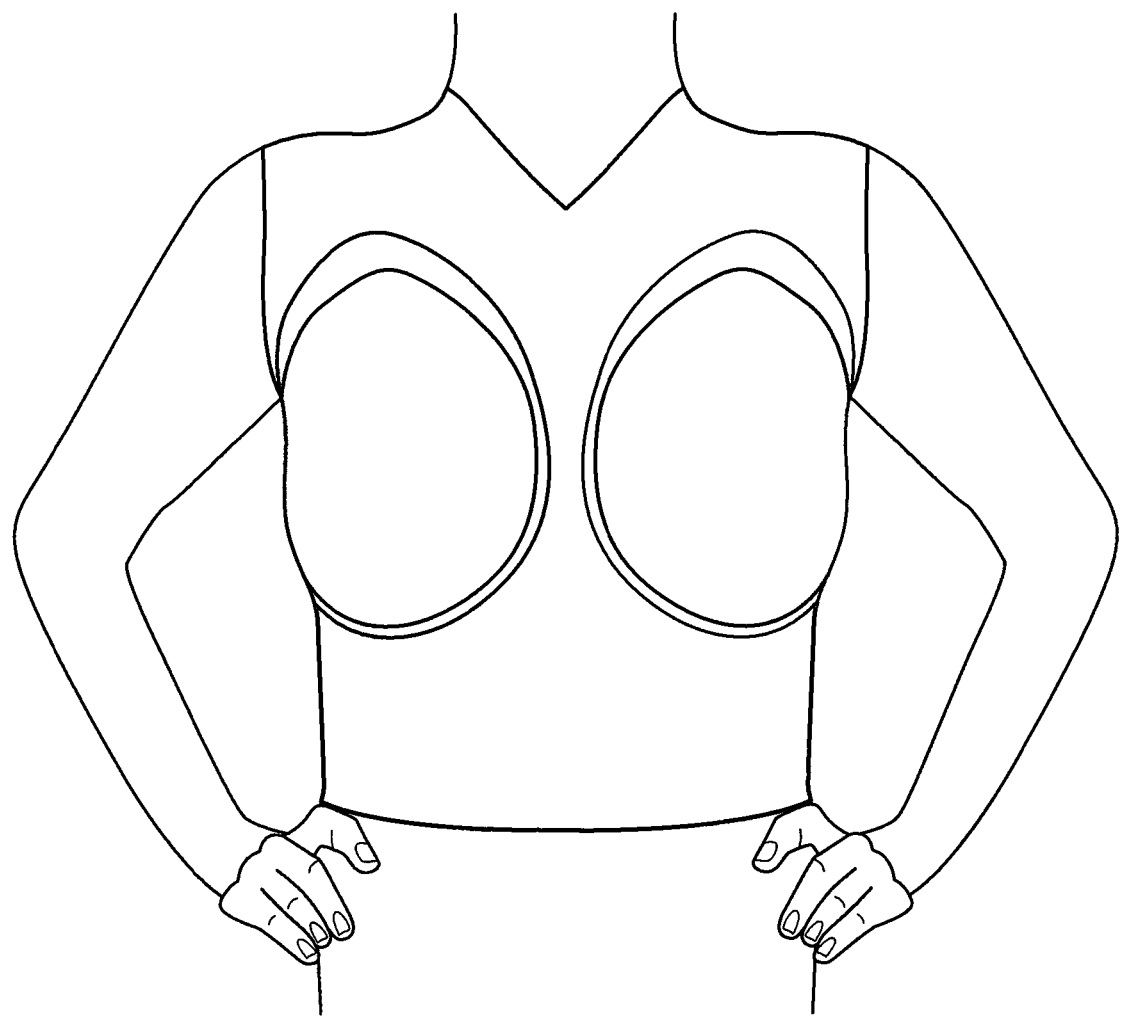
Figure 4C:
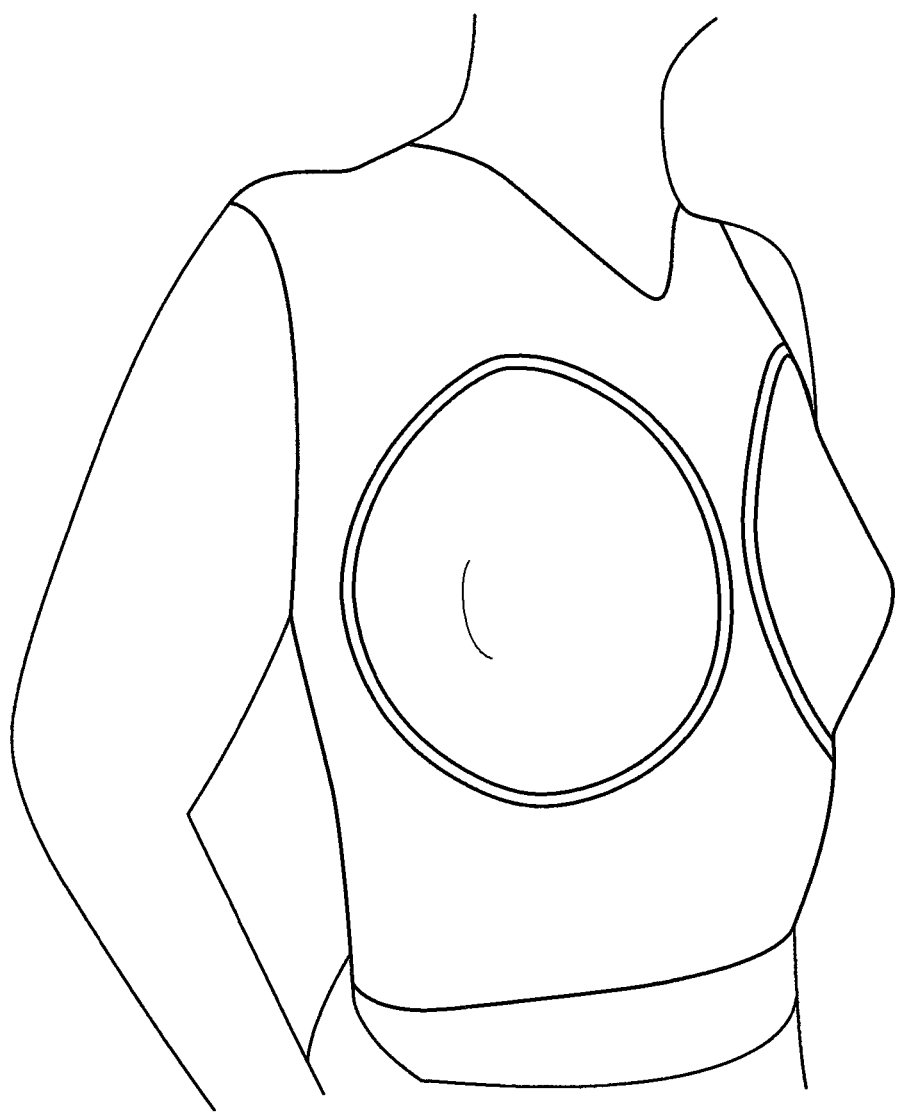
Figure 4D:
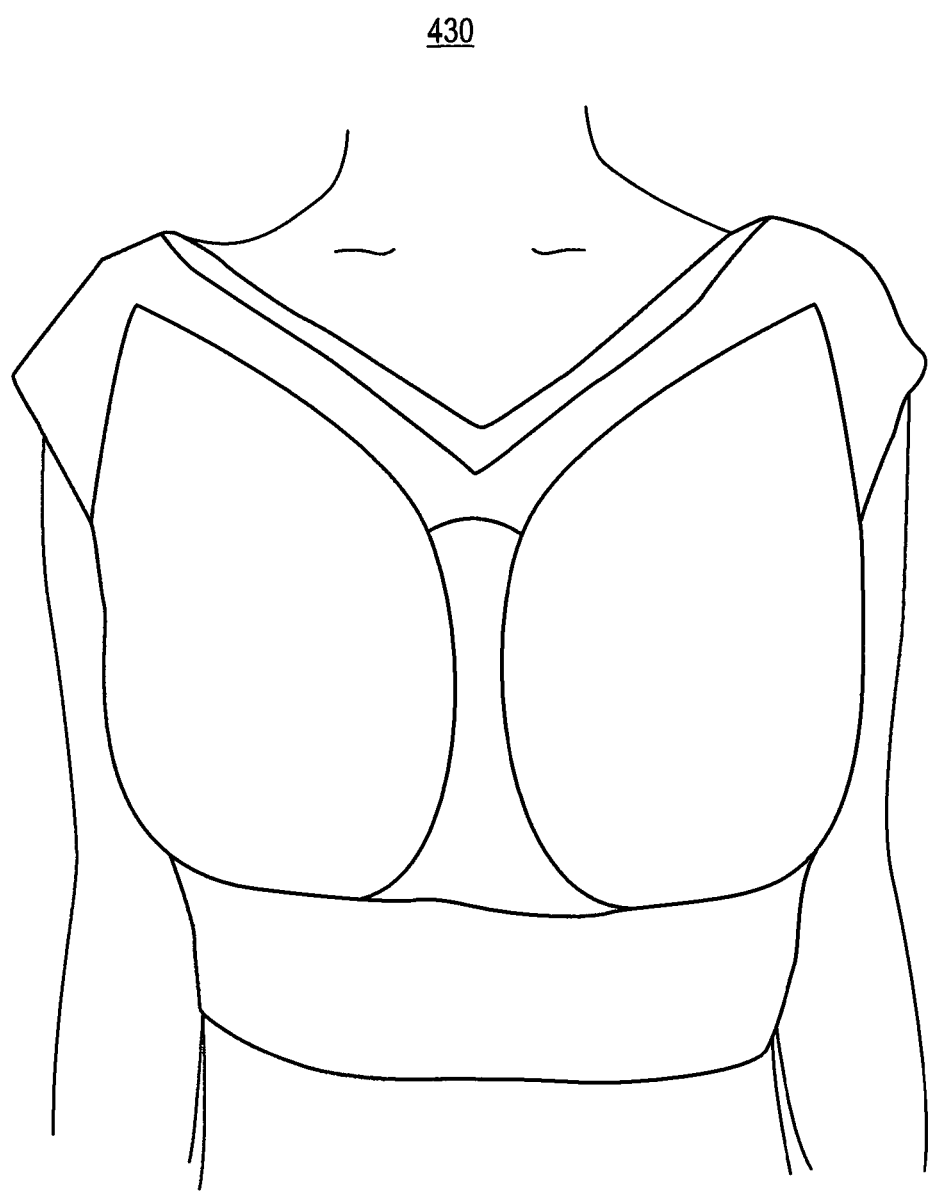

FIGS. 4B, 4C, and 4D are further images of exemplary implementations 410, 420, and 430, respectively, of a brassiere (such as brassiere 300 of FIG. 3) incorporating a rigidifying brace, such as brace 100 of FIG. 1. As shown in implementations 410, 420, and 430 of FIGS. 4B, 4C, and 4D, respectively, the brassiere may include a peripheral shirt-like extension (e.g., comprising a fabric, whether woven, extruded, or the like, or any other polymer or compatible material) that conforms to the torso and is configured to prevent airflow between the inner surface of the cups and the skin of the breasts.

Figure 4E:
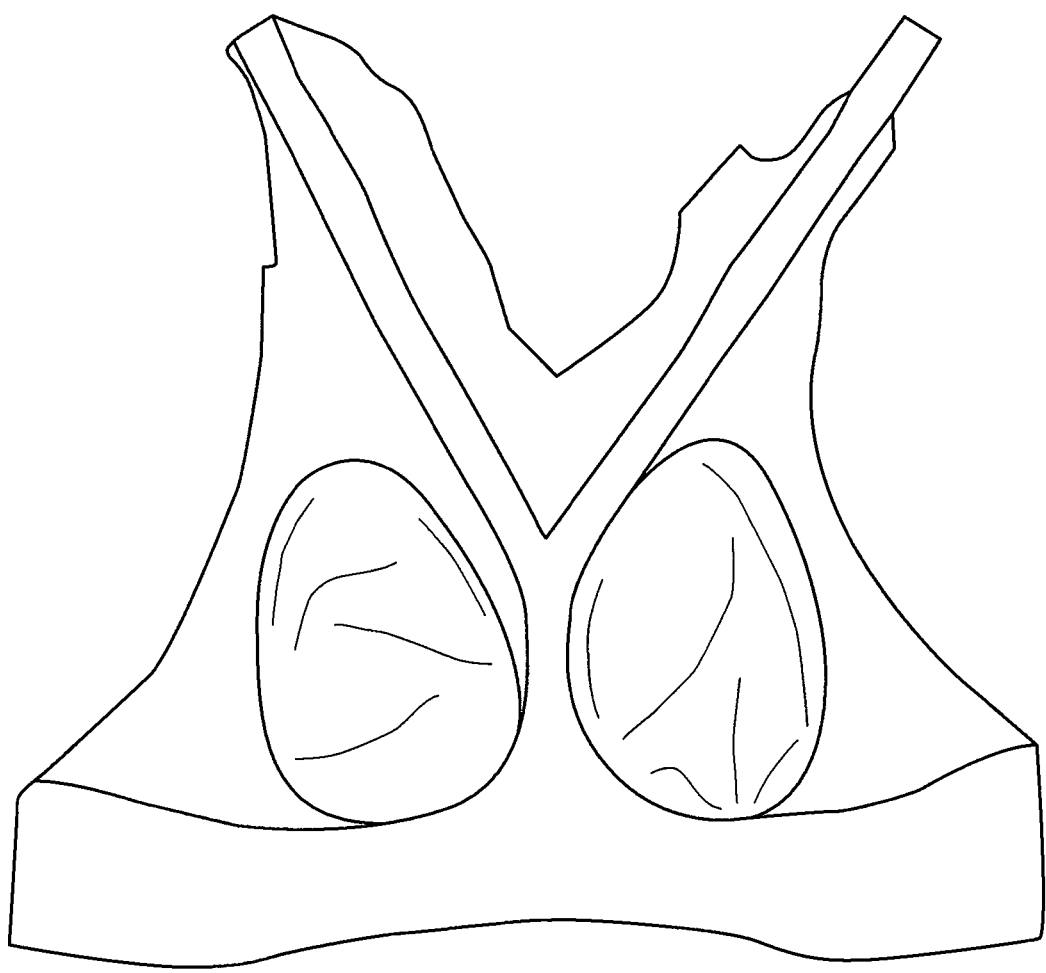

FIG. 4E is a further image of an exemplary implementation 440 of a brassiere (such as brassiere 300 of FIG. 3) incorporating a rigidifying brace, such as brace 100 of FIG. 1, but placed on a table rather than on a body of an individual as depicted in implementations 410, 420, and 430 of FIGS. 4B, 4C, and 4D, respectively.

Figure 4F:
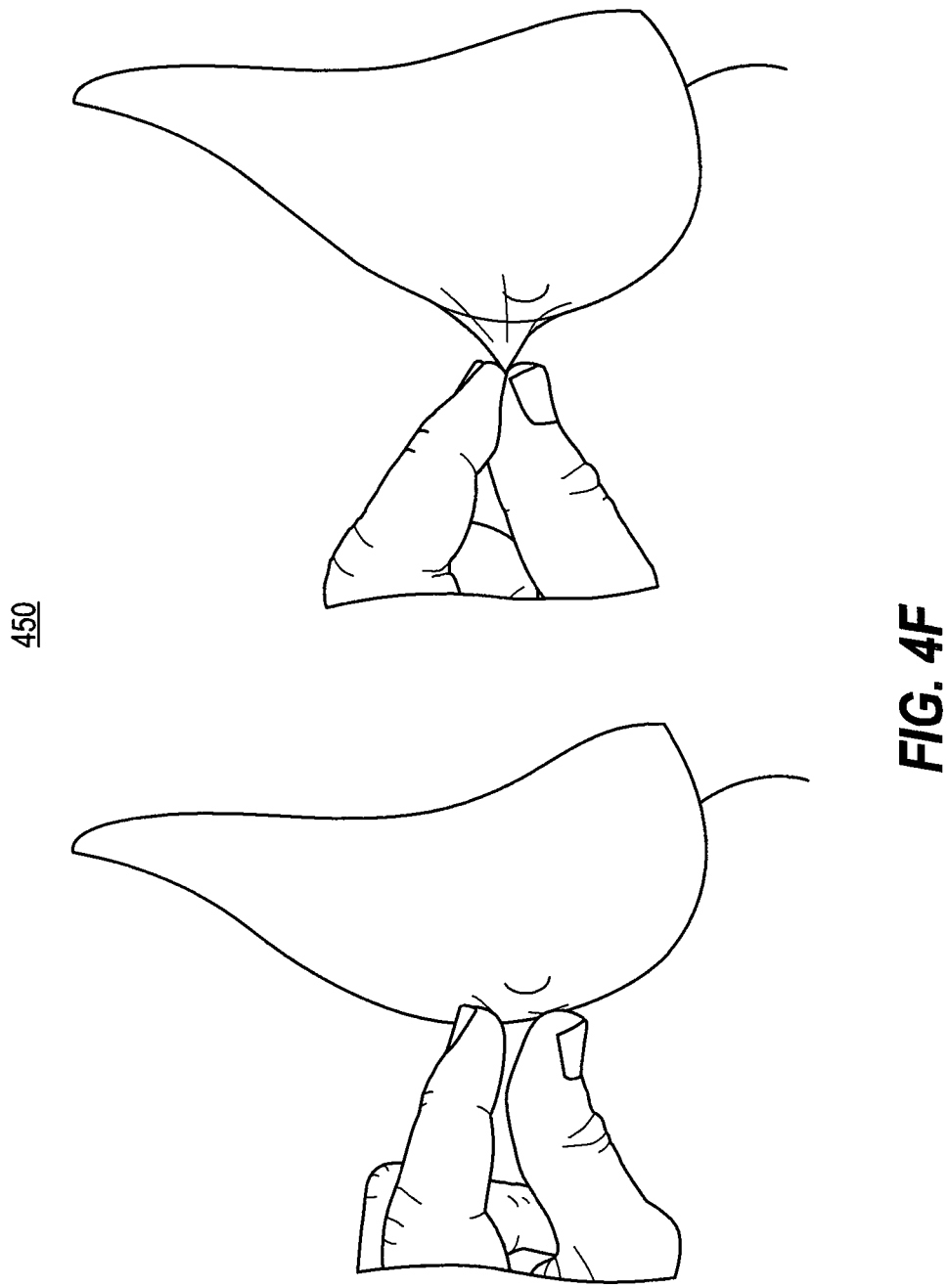

FIG. 4F is an image of an exemplary implementation 450 of a brassiere (such as brassiere 300 of FIG. 3) incorporating a rigidifying brace, such as brace 100 of FIG. 1 using surface tension to adhere to an external surface of a breast. As shown in FIG. 4F, adhesion between the inner layer and the skin of the breast is achieved via surface tension. For example, a thin layer of fluid with high surface tension coefficient, such as water, can provide sufficient adhesive force. Surface tension may adhere while allowing the tissues of the breast to glide and thus avoid potential shear forces. Surface tension also may reduce a need for any adhesive substance that might irritate the skin of the breast. Furthermore, surface tension may be reapplied as described below with respect to method 500 of FIG. 5.

Additionally or alternatively, the cups may adhere to the breasts by using a vacuum, such as by aspirating air between the inner layer and the skin of the breasts and/or by allowing the inner layer to be porous and/or have fine holes such that the vacuum created in the middle layer of the cups also adheres the skin of the breasts to the inner layer.

Additionally or alternatively, the inner layer may adhere to the skin using a pressure sensitive adhesive and/or other types of glue. In such embodiments, the inner layer may be impermeable to the air or fluid in the middle layer.

Figure 4G:
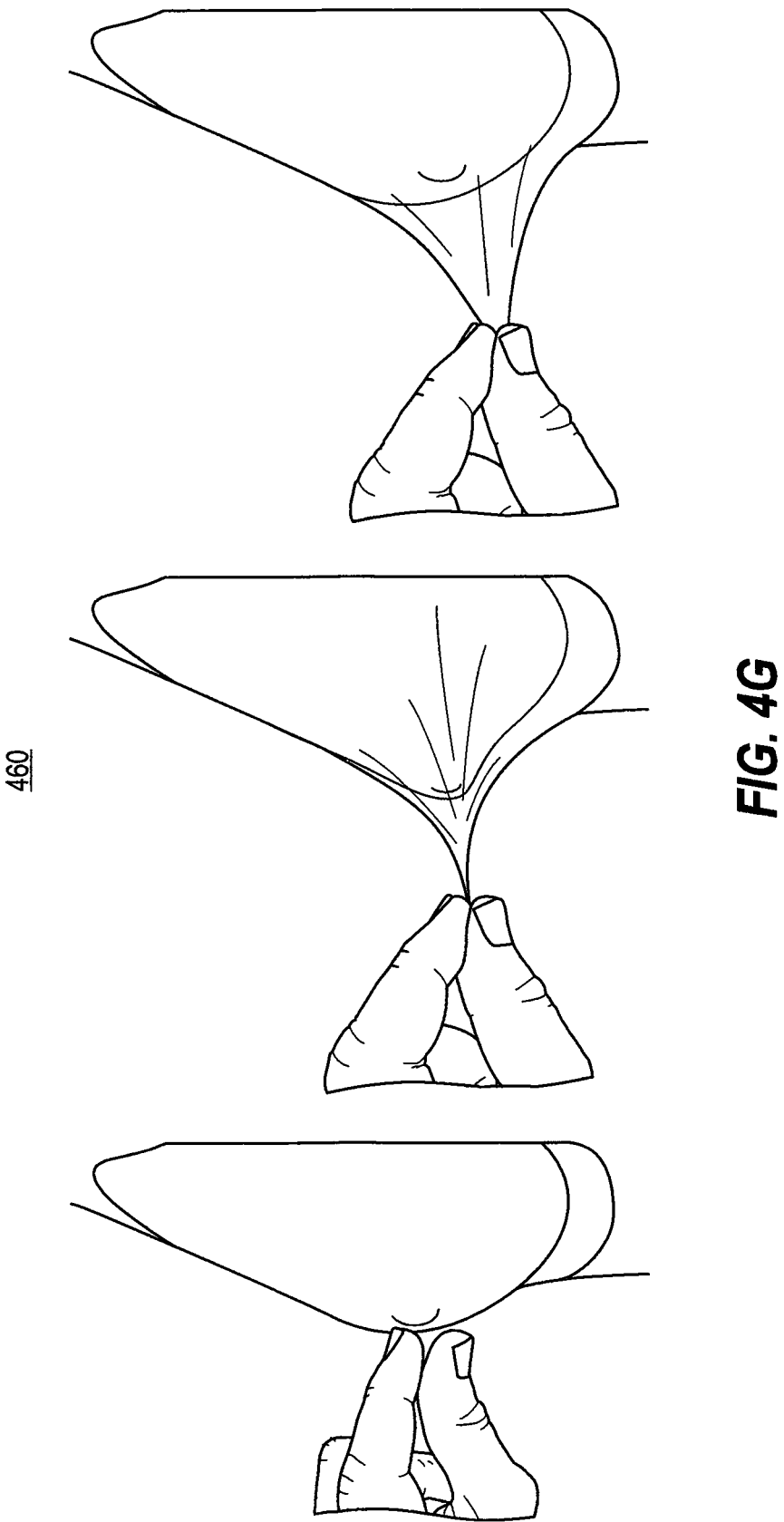

FIG. 4G is an image of an exemplary implementation 460 of a brassiere (such as brassiere 300 of FIG. 3) incorporating a rigidifying brace, such as brace 100 of FIG. 1 showing airflow between the inner layer of the brace and the external surface of the breast. As shown in the example of FIG. 4G, airflow between the inner layer of the brace and the external surface of the breast may cause a reduction in, or even loss of, surface tension between the brassiere and the breast. Embodiments using an adhesive layer (e.g., as shown in FIG. 3B) may retain adhesion even in the event of such airflow. Moreover, as described below with respect to method 500 of FIG. 5, a sensor may monitor air pressure between the inner layer of the brace and the external surface of the breast to allow for remedial measures to be taken if airflow, like that shown in FIG. 4G, causes a reduction in, or even loss of, surface tension.

Figure 5:
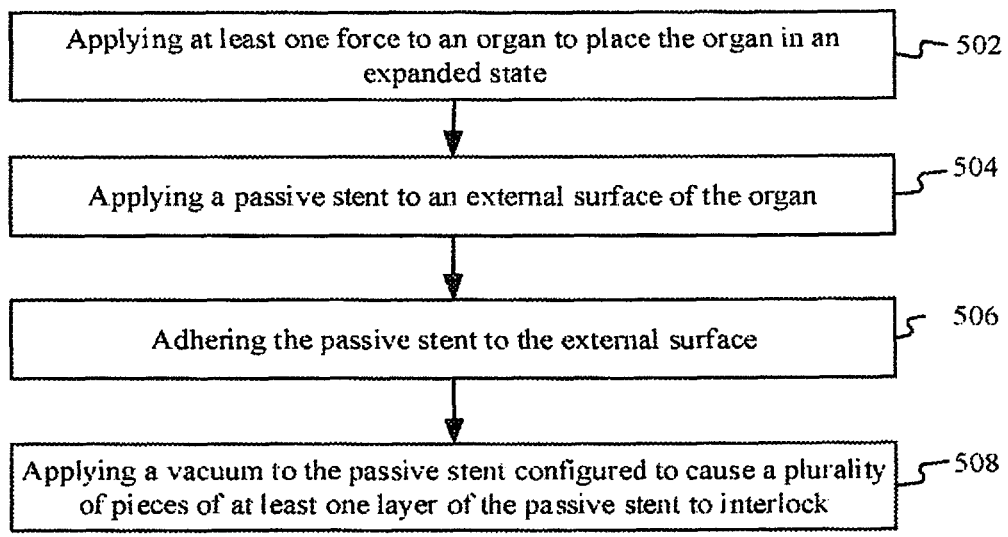
FIG. 5 is a flowchart of an exemplary method for retaining an organ in an expanded state, according to the present disclosure.

FIG. 5 is a flowchart of exemplary method 500 for retaining an organ in an expanded state. Method 500 may be performed using the rigidifying brace 100 as depicted in FIG. 1. Method 500 may also be performed using any of the brassieres disclosed above (e.g., as shown in FIGS. 3A-3C).

At step 502, at least one force is applied to the organ to place the organ in the expanded state. For example, a physiologic solution may be injected in the desired area. The physiologic solution may comprise a vasoconstrictive agent. In some embodiments, the physiologic solution may further comprise an anesthetic, a bonding agent, and/or a rejuvenating agent. In some embodiments, the physiologic solution may comprise a sclerosing agent, e.g., Doxycycline, and/or a tissue glue. In some embodiments, the physiologic solution may be injected via an infusion catheter. In some embodiments, the physiologic solution may be distributed evenly over the area, for example, by moving the catheter during injection.

Additionally or alternatively, a distractive force may be applied to the organ. For example, a vacuum, surface tension, or other external force may induce distention in the organ. In some embodiments, the Brava Bra (see, for example, U.S. Pat. Nos. 5,536,233; 5,662,583; 5,676,634; 5,695,445; 5,701,917; 6,478,656; 6,500,112; 6,641,527; and 6,699,176, all of which are incorporated herein by reference) and/or an external passive expander splint (see, for example, U.S. Pat. Nos. 9,066,795 and 9,522,058) may induce the distractive force and, over a period of time, place the organ in the expanded state.

At step 504, a passive stent is applied to an external surface of the organ. For example, the passive stent may comprise an inner layer in contact with the external surface, an outer layer opposite the inner layer, and a middle layer between the inner layer and the outer layer, as described above and depicted in FIGS. 1 and 2. Accordingly, the passive stent may be configured to substantially conform to the external surface before the middle layer of the same undergoes interlocking.

At step 506, the passive stent is adhered to the external surface. For example, an adhesive, such as tissue glue, may be applied between the inner layer of the stent and the external surface of the organ, as depicted in FIG. 3B.

In some embodiments, applying and adhering the stent may be performed simultaneously. For example, a physician may apply the stent with the adhesive layer such that the inner layer of the stent conforms to the external surface of the organ while the adhesive layer simultaneously adheres the inner layer to the external surface of the organ.

In other embodiments, method 500 may be performed without step 506—that is, without adhering the passive stent. For example, upon application of the vacuum in step 508, surface tension between an external surface of the organ and the inner layer of the stent may adhere the stent to the external surface (e.g., as shown in FIG. 4F) without any additional or separate adhering. Accordingly, in such embodiments, step 508 of method 500 (described below) may be performed after step 504.

At step 508, a vacuum is applied to the passive stent configured to cause a plurality of components of at least one layer of the passive stent to interlock. For example, a port through the inner layer and/or the outer layer may allow for application of the vacuum. The port may be self-sealing after application of the vacuum or may include a removable seal.

Exemplary method 500 may comprise additional steps. For example, method 500 may comprise monitoring an air pressure between the external surface of the organ and the inner layer. For example, a barometer, piezoelectric sensor, or any other device for measuring air pressure may monitor the volume between the external surface of the organ and the inner layer. In such embodiments, an indication of an increase in air pressure based on the monitoring may trigger remedial action. For example, in embodiments where a vacuum is used, at least in part, to adhere the inner layer to the external surface, a pump may automatically apply additional suction to the volume between the external surface of the organ and the inner layer to remedy a reduction in or loss of surface tension. Alternatively, a physician or user may receive an alert in response to the indication of increase in air pressure and apply additional suction using a vacuum to remedy a reduction in or loss of surface tension. In embodiments where only surface tension between the external surface of the organ and the inner layer is used for adhering the same, a pump may still be used as described above to remedy a reduction in or loss of that surface tension.

The foregoing description has been presented for purposes of illustration. It is intended that the specification and examples be considered as exemplary only. It is not exhaustive and is not limited to precise forms or embodiments disclosed. Other embodiments will be apparent to those skilled in the art from consideration of the specification and practice of the embodiments disclosed herein. Modifications and adaptations of the embodiments will be apparent from consideration of the specification and practice of the disclosed embodiments.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

What is claimed is:

1. A brassiere comprising:
   two cups, each configured to support a breast and each comprising:
   an inner layer;
   an outer layer;

a middle layer enclosed by the inner layer and the outer layer and comprising a plurality of components configured to interlock upon application of a vacuum; and a port configured for applying the vacuum to the middle layer;

wherein the middle layer is configured to substantially conform to an external surface of the breasts after interlocking, and wherein the middle layer is configured to maintain the breasts in the expanded state after interlocking.

2. The brassiere of claim 1, further comprising a semi-rigid frame and configured to secure the two cups to the breasts.

3. The brassiere of claim 1, further comprising an extension surrounding at least a portion of the two cups and configured to block airflow between the inner layer and skin of the breasts.

4. The brassiere of claim 1, further comprising fabric configured to conform to a torso and block airflow between the inner layer and skin of the breasts.

5. The brassiere of claim 1, wherein the inner layer is configured to adhere to the breasts using surface tension.

* * * * *